US009182344B1

(12) United States Patent
Mitchell

(10) Patent No.: US 9,182,344 B1
(45) Date of Patent: Nov. 10, 2015

(54) DEVICE FOR THE DETECTOR OF FOULING ON OPTICAL SURFACES OF A NEPHELOMETRIC TURBIDIMETER SUBMERGED IN A LIQUID

(71) Applicant: Herbert Mitchell, Grand Junction, CO (US)

(72) Inventor: Herbert Mitchell, Grand Junction, CO (US)

( * ) Notice: Subject to any disclaimer, the term of this patent is extended or adjusted under 35 U.S.C. 154(b) by 0 days.

(21) Appl. No.: 14/544,028

(22) Filed: Nov. 18, 2014

(51) Int. Cl.
*G01N 21/53* (2006.01)

(52) U.S. Cl.
CPC .......... *G01N 21/53* (2013.01); *G01N 2201/061* (2013.01); *G01N 2201/0642* (2013.01)

(58) Field of Classification Search
CPC ...... G01N 21/51; G01N 21/53; G01N 21/532
USPC .......................................................... 356/338
See application file for complete search history.

(56) References Cited

U.S. PATENT DOCUMENTS

| | | | | |
|---|---|---|---|---|
| 4,896,047 A * | 1/1990 | Weaver | ................. | G01N 21/534 250/239 |
| 5,185,333 A * | 2/1993 | Kawakita | ............. | C07D 265/36 514/224.2 |
| 5,185,533 A * | 2/1993 | Banks | ................. | G01B 11/0616 250/301 |
| 5,796,478 A * | 8/1998 | Wetegrove | ......... | G01N 21/6486 250/458.1 |
| 6,023,070 A * | 2/2000 | Wetegrove | ........... | G01N 21/532 250/573 |
| 6,894,778 B2 * | 5/2005 | Palumbo | ................ | G01N 21/51 356/338 |
| 7,142,299 B2 * | 11/2006 | Tokhtuev | ................ | G01N 21/53 356/338 |
| 7,659,980 B1 * | 2/2010 | Mitchell | ............ | G01N 21/4785 356/338 |
| 8,144,330 B2 * | 3/2012 | Itoh | ........................ | G01N 21/94 356/446 |
| 8,345,248 B2 * | 1/2013 | Hong | ................... | G01N 21/534 356/436 |
| 8,488,122 B2 * | 7/2013 | Dong | ..................... | G01N 21/53 356/445 |
| 2002/0010891 A1 * | 1/2002 | Klein | ................... | G06F 11/1008 714/767 |
| 2003/0214653 A1 * | 11/2003 | Palumbo | ................ | G01N 21/51 356/338 |
| 2005/0168741 A1 * | 8/2005 | Banks | .................. | G01N 21/645 356/417 |
| 2006/0103842 A1 * | 5/2006 | Tokhtuev | ............... | G01N 21/53 356/338 |
| 2006/0262309 A1 * | 11/2006 | Banks | .................. | G01N 21/645 356/417 |
| 2013/0003048 A1 * | 1/2013 | Caussin De Schneck | ................ | B01D 65/10 356/72 |

* cited by examiner

*Primary Examiner* — Roy M Punnoose

(57) ABSTRACT

Describes a device which embodies a method of providing a periodic test light-source beam directed at a nephelometric turbidimeter's scattered-light detector window to detect any film build-up on the scattered-light detector's optical surfaces by means of a change in reading from a previous reading.

1 Claim, 1 Drawing Sheet

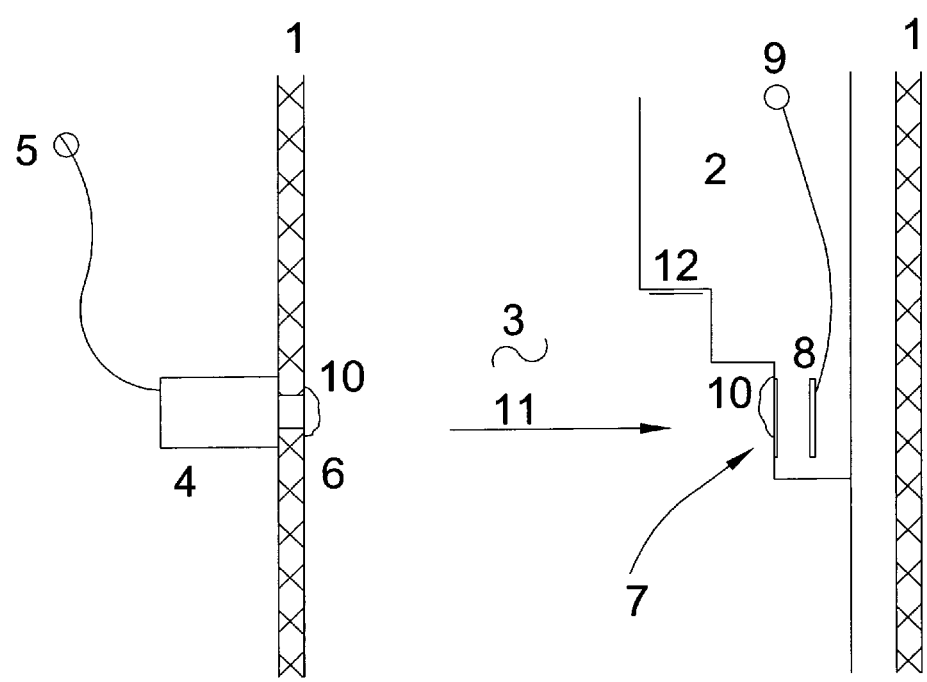

DEVICE FOR THE DETECTOR OF FOULING ON OPTICAL SURFACES OF A NEPHELOMETRIC TURBIDIMETER SUBMERGED IN A LIQUID

CROSS-REFERENCE CITED AS RELATED APPLICATION

U.S. Patent Document
U.S. Pat. No. 7,659,980 B1—NEPHELOMETRIC TURBIDITY SENSOR DEVICE
September 2010 Mitchell et al.
U.S. Cl 356/339

The USEPA required the U.S. patent referenced above be used in conjunction with USEPA specifications for Mitchell Method M5331: DETERMINATION OF TURBIDITY BY LED NEPHELOMETRY and for Mitchell Method M5271 DETERMINATION OF TURBIDITY BY LASER NEPHELOMETRY; both published in the Federal Register Aug. 3, 2009. The instant patent application was requested by the USEPA to be used in conjunction with the referenced Mitchell U.S. Pat. No. 7,659,980, which is incorporated herein by reference. This inventor's instant device displays any changes in optic clarity from a previous reading. It is important to know when a change in turbidity has occurred, and to know whether this change was due to optic surface fouling or to changes in the actual water condition.

TECHNICAL FIELD OF THE INVENTION

Water treatment plants, waste water treatment plants, and other liquid process systems using nephelometric turbidimeters to measure particulate concentration in the liquid flow may encounter obscurence of light due to film build-up on optical windows. This attenuation of light decreases the reliability of the turbidity measurement and must be corrected in some manner.

BACKGROUND OF THE INVENTION

Current detection of film build-up on optical windows in nephelometric turbidimeters is primarily by visual inspection. The particulate response of the turbidity measurement provides a possible clue that build-up and fouling of the optical surfaces may be a cause of the change in unexpectedly low readings of the turbidity response. Attenuation of light caused by fouling of optical surfaces is reflected in lower readings than expected for the actual turbidity concentration.

The USEPA is in the process of changing their procedures to incorporate newer technology around the use of LED and laser light sources, with reference to this inventor's U.S. Pat. No. 7,659,980 B1. These stated light sources are more stable in their output than the older incandescent light sources with their drifting filaments. Associated electronics have also advanced in recent years in the capability to control source light stability through better feedback circuitry.

In order to complete these changes in the EPA procedures and specifications, the EPA recommended that detection for specific film build-up on optical surfaces be a part of the new procedure specifications required for nephelometric turbidity measurement used in water and waste water treatment plants. The patents and accompanying EPA Mitchell Methods M5331 and M5271 addressed drifting in the instruments cited in the Methods and patent above.

Under the older U.S. specifications, primarily using incandescent light sources, plant operators found that only after cleaning of the optical surfaces was a more accurate determination of the measurement response possible. In most incandescent instruments, visual inspection of the optical surfaces requires a breakdown of the instrument in order to determine if build-up has occurred.

Elimination of film build-up on optical windows by plant operators may include: automatic wipers, ultrasonic vibration, air or water jets, and/or disassembly of the unit so that windows can be wiped or cleaned manually. Unfortunately, each of these methods is incomplete in fully removing film build-up, giving a false interpretation of the window's actual cleanliness. In addition these intrusive methods allow unintended changes in the water condition, which then affects an accurate response reading. The object of the present device is to assist the operator in making a better decision about the accuracy of turbidity responses in regards to the attenuation of its light source due to fouling on optical surface(s).

Below is a comparison between the instant invention with patents or patent applications which provide various additional approaches to detection of fouling on optical surfaces. None of these approaches, using scattered-light sensors, use this inventors' unique nephelometric turbidity scattered-light sensor design.

There are a number of prior-art patents suggesting ways to detect fouling in instrumentation in fluid/liquid conditions. U.S. Pat. No. 6,023,070 describes use of a plastic conduit measuring absorbance of the light beam. Control of the beam intensity, detector sensitivity and associated electronics were not included. Two areas of the tube, one fouled and one un-fouled, was measured and compared by the device. This method is not appropriate for use with this inventor's fouling detection device, which is to be used in conjunction with the cited Mitchell patent covering the inventor's nephelometric turbidimeter, functioning in the absorption mode, in which all areas are fouled.

U.S. Patent Application 2002/0108911A1 measures fouling by having two sensors in the fluid; one that has been allowed to foul and a second one that has been cleaned—then measured and compared after re-immersion in the fluid. There is no mention in this patent control of the beam intensity, detector sensitivity and associated electronics. This method is not appropriate for use with this inventor's fouling detection device, which is to be used in conjunction with the cited Mitchell patent covering the inventor's nephelometric turbidimeter, functioning in the absorption mode, in which all areas are fouled.

Another approach found in U.S. Pat. No. 5,185,333 describes a method of measuring fouling by using two sensors; one allowed to foul and the other periodically cleaned. The light transmitted from one side of the container is compared to the opposite side. Again, there is no mention of control of the beam intensity, detector sensitivity and associated electronics. This method is not appropriate for use with this inventor's fouling detection device, which is to be used in conjunction with the cited Mitchell patent covering the inventor's nephelometric turbidimeter, functioning in the absorption mode, in which all areas are fouled.

U.S. Pat. No. 4,896,047 describes a method of measuring gas-stack fouling by successive cleaning and measuring the absorbance of a light beam across the stack and checking for changes. There is no mention of control of the beam intensity, detector sensitivity and associated electronics. This method is not appropriate for use in water or liquid with this inventor's fouling detection device, which is to be used in conjunction with the cited Mitchell patent covering the inventor's nephelometric turbidimeter, functioning in the absorption mode, in which all areas are fouled.

An additional approach in U.S. Patent Application 2013/0003048A1 describes a method similar to the present device but with restrictions which substantially differ:

Claim 14 describes an optical method for measuring the optical transparency of the fluid in a fluid treating device as a means of measuring fouling of surfaces in contact with the fluid. The device measures the transparency of the fluid at two locations, one fouled and one un-fouled. This method is not appropriate for use with this inventor's fouling detection device, which is to be used in conjunction with the cited Mitchell patent covering the inventor's nephelometric turbidimeter, functioning in the absorption mode, in which all areas are fouled.

Claim 17 describes use of a light source for measuring the optical transparency described in claim 14 by use of a light source, transparent window, said fluid, and an optical detector, which is immediately adjacent to the light source window, to detect light scattered by the fouling on the transparent window. This method is not appropriate for use with this inventor's fouling detection device which is to be used in conjunction with the cited Mitchell patent covering the inventor's nephelometric turbidimeter, functioning in the absorption mode, as it would be mechanically and optically impossible to position the measurement device in the stated adjacent position.

Claim 19 describes: (a) Measures the transparency of the fluid for changes in transparency which indicates a change in the fouling of the surfaces. Without control of changes in the light source, changes in the detector and its electronics, which are not mentioned, this approach would not be appropriate for use with this inventor's fouling detection device which is to be used in conjunction with the cited Mitchell patent covering the inventor's nephelometric turbidimeter functioning in the absorption mode.

(b) claim 19 describes use of an equation in the determination of the fouling parameter. A mathematical equation would not be appropriate for incorporation of the present device in this inventor's fouling detection device, which is to be used in conjunction with the cited Mitchell patent covering the inventor's nephelometric turbidimeter, as its device detector, under electronic control, is also the nephelometric turbidity detector, but functioning in the absorption mode.

(c) Measurement within a fouled location compared with measurement of an unaffected location quantifies the level of fouling in Claim 19. Use in this inventor's fouling detection device, which is to be used in conjunction with the cited Mitchell patent covering the inventor's nephelometric turbidimeter, functioning in the absorption mode, would be inappropriate as fouling in this instant device is displayed only in reference to a previous reading and is not quantified by the level of fouling. Claim 19 describes the level of fouling, while this instant invention describes any change in fouling from the last time it was checked.

There are additional factors potentially affecting the response reading. Three of these are stated below to clarify that they have been eliminated or were not factors which needed to be overly considered. Items 1 and 2 were covered in the above cross-referenced sensor design. Item 3 is negligible due to the EPA ruling for variance:

Light Source Attenuation Factors Which Were Previously Resolved in the Cross-Referenced Design and/or Patent, or by the EPA Ruling of Variance:

1. Variation in the source light of the cross-referenced sensor device is controlled by electronic feedback circuitry, removing this as a factor.

2. Changes in sensitivity of the scattered-light detector and its associated electronics were eliminated by use of the Mitchell Self-Check circuit described in the above cross-referenced U.S. patent, removing this as a factor.

3. Attenuation of the light beam passing through particulate matter in the liquid lowers the response reading. Common usage references indicate that a 100 NTU (Nephelometric Turbidity Units) liquid of particulate density through a 10 cm path length has a light loss of 10%. The cross-referenced sensor device was designed with a path length of 4 cm, (EPA specifications limit nephelometric turbidity Methods to 40 NTU) therefore a change in light loss of 1.6% is negligible. The EPA allows a 10% variance, removing this as a factor.

The Two Elements of Focus for the Present Device:
Fouling of the test source-light window, which essentially cannot be eliminated, but acts as a surrogate detection for fouling of the operating source-light window;
Fouling of the scattered-light detector window.

USEPA *Guidance Manual for Compliance with the Interim Enhanced Water Treatment Rule: Turbidity Provisions*, state: "If the instrument has internal electronic diagnostics, designed to assist in determining proper calibration, the operator should use these tools to verify proper calibration operation." The rules continue to state that "the unit should be thoroughly cleaned."

Determination of fouling of optical windows and fouling elimination falls under this directive. Unfortunately, there is no current system designed to determine fouling on optical windows accept as described above. It is the object of this present device to provide a means of determination of fouling, internal to the nephelometric turbidity system, without disassembling the unit manually for visual inspection.

Internal detection of fouling can be automatic or placed on a periodic schedule by the operator. It has been shown that keeping windows clean is more efficient and effective than cleaning a window after it has become fouled. The object of this present device is to provide a means of determining fouling, or absence of fouling, on a periodic basis, or as needed when the water condition changes. The water plant operator has this data at his disposal 24/7, to a degree far more effective than visual inspection can provide.

Cross-Referenced Patent with the Present Device: Application and use of the present device is to be used in conjunction with the Nephelometric Turbidity Sensor Device referenced in U.S. Pat. No. 7,659,980 B1. The purpose of this present device is to assist the plant operator in determining if the accuracy of the turbidimeter response reading is being affected by fouling on the optical window(s) either by organic or non-organic processes, without increasing contamination of the water condition through manual inspection.

BRIEF SUMMARY OF THE INVENTION

Elimination of the three fouling components listed above was responded to in the original designs of the cross-referenced patent, or by the EPA ruling for variance. However, interpretation of the variations in the light source signal would be incomplete without also detecting (1) fouling on the test light-source window, which acts as a surrogate for the operating window and its potential fouling, and also, (2) fouling on the scattered-light detector window. Since three of the fouling components were eliminated in the Nephelometric Turbidity Sensor design and patent, or by the EPA ruling on variance, only the two remaining fouling components are of interest using this present device. Prior art has provided a number of approaches to detection of fouling on optical surfaces. This inventor's unique approach using a nephelometric turbidity sensor is to compare a current reading from the sensor with previous readings, providing a detection of change, but not the level of change, only that something has changed, which may be either fouling of the window or a change in the water condition. Negative change from the previous reading suggests that the change is directly related to fouling of the window. Absorption of light, as opposed to scattered light against particulate matter traveling through the sample water, is negligible. Since absorption is negligible, any lowering of the scattered light detector signal would indicate a fouling of the optical surfaces. This inventor's approach is to use the scattered light detector to measure absorption by switching its mode from nephelometric measurement to absorption measurement, as a function of its associated electronics.

FIGURE NUMBER OF THE DRAWING WITH DESCRIPTION

FIG. 1 describes a present device for fouling detection

REFERENCE NUMBERS WITH DESCRIPTION

FIG. 1

1. chamber wall
2. sensor body
3. liquid
4. light source
5. light source control
6. light source window
7. scattered-light detector window
8. scattered light detector
9. scattered-light detector electronics
10. fouling material
11. light beam
12. turbidity light-source window

DETAILED DESCRIPTION OF THE INVENTION

Referring to the drawing (FIG. 1) there are a number of embodiments set forth which will be described with respect to each part of the drawing wherein like numerals represent like components.

Flow chamber walls 1 containing within it a liquid 3. The sensor body 2, immersed in the liquid 3 inside the flow chamber walls 1, is sealed. The sensor body 2 has a turbidity light source window 12, a scattered light-detector window 7, a scattered-light detector 8 along with its associated electronics 9.

The detector light source 4 attached to the wall of the flow chamber 1 has a reference signal controlling a light beam 11. The light beam 11 exits through the flow chamber wall 1 via the light source window 6. The detector light source 4 is controlled by the feedback electronics 5 which gets its reference signal from inside the detector light-source 4.

The detector light source 4 generates the light beam 11 which passes through the detector light-source window 6, the fouling material 10 on that window, the liquid being measured 3, and the fouling material 10 passing through the scattered-light detector window 7, and onto the scattered-light detector 8, which converts the light beam 11 into an electrical signal which is transmitted to the scattered light electronics 9 to provide a reading. This gives an indication of the level of the fouling material 10 on the detector light-source window 6 and on the scattered light-source window 7.

The detector light-source 4 is held constant by the light source electronics 5. The scattered light detector 8 and its electronics 9 are held constant by the Self-Check circuitry described in U.S. Pat. No. 7,659,980. Changes in the turbidity of the liquid 3 are insignificant to affect readings or changes in the level of the light beam 11 passing through it, leaving only fouling material 10 on the detector light-source window 6, and the fouling material 10 on the scattered light-detector window 7, as variables for detection of fouling.

What is claimed is:

1. A device for detection of fouling on optical surfaces of a nephelometric turbidimeter submerged in a liquid, said device comprising:
   a walled flow chamber containing said liquid;
   a light source mounted at a light emission window on said chamber wall and configured to emit a light beam through said liquid, said light source connected to and controlled by feedback light-emission electronics to maintain a constant light output;
   a sealed sensor body having a scattered-light detection window and a scattered-light detector, said scattered-light detector connected to light detection electronics and configured to convert incident light beam into an electrical signal to provide a measurement reading indicating fouling material on the optical surfaces of said light emission and light detection windows, and said light detection electronics in absorption mode configured to compare output of the scattered-light detector with a previous reading to determine any change in a subsequent reading to indicate fouling on said optical surfaces.
wherein,
   said light source is configured to emit and direct a light beam through said light emission window, said liquid and through said light detection window to said scattered-light detector;
   said detection window and said scattered-light detector are on opposing side of said light source and light emission window.

* * * * *